(12) United States Patent
Rabello et al.

(10) Patent No.: US 8,525,993 B2
(45) Date of Patent: Sep. 3, 2013

(54) SCATTEROMETRY MEASUREMENT OF ASYMMETRIC STRUCTURES

(75) Inventors: Silvio J. Rabello, Palo Alto, CA (US); William A. McGahan, Spicewood, TX (US); Jie Li, Milpitas, CA (US); Yongdong Liu, Cupertino, CA (US)

(73) Assignee: Nanometrics Incorporated, Milpitas, CA (US)

( * ) Notice: Subject to any disclaimer, the term of this patent is extended or adjusted under 35 U.S.C. 154(b) by 591 days.

(21) Appl. No.: 12/696,974

(22) Filed: Jan. 29, 2010

(65) Prior Publication Data

US 2011/0080585 A1 Apr. 7, 2011

Related U.S. Application Data

(60) Provisional application No. 61/260,314, filed on Nov. 11, 2009, provisional application No. 61/249,439, filed on Oct. 7, 2009.

(51) Int. Cl.
*G01J 4/00* (2006.01)

(52) U.S. Cl.
USPC .......................................... 356/368; 356/369

(58) Field of Classification Search
USPC ........... 356/364–370, 601–636, 237.1–237.5; 250/214.1, 214 R
See application file for complete search history.

(56) References Cited

U.S. PATENT DOCUMENTS

| | | | |
|---|---|---|---|
| 4,053,232 A | 10/1977 | Dill et al. | |
| 4,884,886 A * | 12/1989 | Salzman et al. | 356/367 |
| 6,819,426 B2 * | 11/2004 | Sezginer et al. | 356/401 |
| 6,947,141 B2 | 9/2005 | Bischoff et al. | |
| 6,949,462 B1 | 9/2005 | Yang et al. | |
| 6,982,793 B1 | 1/2006 | Yang et al. | |
| 6,992,764 B1 | 1/2006 | Yang et al. | |
| 7,069,182 B2 * | 6/2006 | Johnson et al. | 702/182 |
| 7,218,398 B2 * | 5/2007 | Smith | 356/367 |
| 7,265,850 B2 * | 9/2007 | Archie et al. | 356/625 |
| 7,277,172 B2 | 10/2007 | Kandel et al. | |
| 7,346,878 B1 | 3/2008 | Cohen et al. | |
| 7,515,279 B2 * | 4/2009 | Raymond | 356/601 |
| 7,525,672 B1 * | 4/2009 | Chen et al. | 356/625 |
| 7,791,732 B2 * | 9/2010 | Den Boef et al. | 356/456 |
| 2006/0274310 A1 * | 12/2006 | Kandel et al. | 356/369 |
| 2007/0263219 A1 * | 11/2007 | De Martino et al. | 356/364 |
| 2009/0135416 A1 | 5/2009 | Shchegrov et al. | |

OTHER PUBLICATIONS

Colburn et al., "Characterization and modeling of volumetric and mechanical properties for step flash imprint lithography photopolymers," J. Vac. Sci. Technol. B 19(6), 2685-2689 (2001).

(Continued)

*Primary Examiner* — Sang Nguyen
(74) *Attorney, Agent, or Firm* — Silicon Valley Patent Group LLP

(57) ABSTRACT

Asymmetry metrology is performed using at least a portion of Mueller matrix elements, including, e.g., the off-diagonal elements of the Mueller matrix. The Mueller matrix may be generated using, e.g., a spectroscopic or angle resolved ellipsometer that may include a rotating compensator. The Mueller matrix is analyzed by fitting at least a portion of the elements to Mueller matrix elements calculated using a rigorous electromagnetic model of the sample or by fitting the off-diagonal elements to a calibrated linear response. The use of the Mueller matrix elements in the asymmetry measurement permits, e.g., overlay analysis using in-chip devices thereby avoiding the need for special off-chip targets.

52 Claims, 11 Drawing Sheets

(56) References Cited

OTHER PUBLICATIONS

Collins, et al., "Dual Rotating Compensator," Handbook of Ellipsometry, H.G. Tompkins and E.A. Irene, Eds., William Andrew Publishing & Springer-Verlag, Chap. 7.3.3, 546-547 (2005).

Hedlund, et al, "Microloading effect in reactive ion etching," J. Vac. Sci. Technol. A 12(4), 1962-1965 (1994).

Li, et al., "New formulation of the Fourier modal method for crossed surface-relief gratings," J. Opt. Soc. Am. A 14, 2758-2767 (1997).

Li, et al., "Symmetries of cross-polarization diffraction coefficients of gratings," J. Opt. Soc. Am. A 17, 881-887 (2000).

Novikova et al., "Metrological applications of Mueller polarimetry in conical diffraction for overlay characterization in microelectronics," Eur. Phys. J. Appl. Phys., 31, 63-69 (2005).

Novikova et al., Application of Mueller polarimetry in conical diffraction for critical dimension measurements in mircoelectronics, Applied Optics, 45:16, 3688-3697 (2006).

Raymond, et al., "Asymmetric line profile measurement using angular scatterometry," Proc. SPIE, vol. 4344, 436-446 (2001).

Raymond, "Scatterometry for Semiconductor Metrology," Handbook of silicon semiconductor metrology, A.C. Diebold, Ed., (Academic Press), Chap. 18, 477-514 (2001).

Rochford, "Polarization and Polarimetry," National Institute of Standards and Technology publication, http://boulder.nist.gov/div815/81503_pubs/PPMDocs/Rochford-EPST-02.pdf, 25 pp.

Smith, et al., "Overlay metrology at the crossroads," Proc. SPIE 6922, 0277-0286 (2008).

Vagos, et al., "Uncertainty and Sensitivity Analysis and its applications in OCD measurements," Proc. of SPIE 7272, 72721N-72721N-9 (2009).

Wang, et al., "Template Replication Using a Tone-Reversal Imprint Process for Patterned Magnetic Recording Media," The 7th International Conference on Nanoimprint and Nanoprint Technology, NTT2008.

International Search Report and Written Opinion of the International Searching Authority mailed Nov. 29, 2010, International Application No. PCT/US2010/049878, filed Sep. 22, 2010, 8 pp.

\* cited by examiner

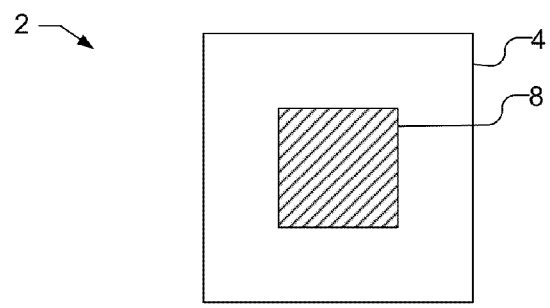
Fig. 1
(Conventional)

SCATTEROMETRY MEASUREMENT OF ASYMMETRIC STRUCTURES

CROSS REFERENCE TO RELATED APPLICATIONS

This application claims the benefit of Provisional Application Nos. 61/249,439 and 61/260,314, filed Oct. 7, 2009 and Nov. 11, 2009, respectively, both of which are incorporated by reference herein in their entirety.

BACKGROUND

Scatterometry has been used extensively for the characterization of critical dimensions (CD) and detailed side-wall profiles of periodic structures in microelectronics fabrication processes. Scatterometry can provide accurate and high-precision measurement for 2D and 3D structures used in integrated circuits. Various experimental configurations, e.g., normal incident broadband reflectance spectroscopy, spectroscopic ellipsometry, and angular scatterometry measurement, have been developed to collect light signals diffracted from periodic structures. So far the majority of measurements were applied for symmetric gratings. In most cases devices are designed to be symmetric although errors could occur during fabrication processing and result in undesired asymmetry.

One example of asymmetry is alignment or overlay error. Typically, overlay targets are used to determine if the pattern produced in one layer is adequately aligned with the pattern in an underlying or previously patterned layer. However, as integrated circuit feature size continues to decrease to provide increasing circuit density, it becomes increasingly difficult to accurately measure the overlay between successive layers. This overlay metrology problem becomes particularly difficult at submicrometer feature sizes where overlay tolerances are reduced to provide reliable semiconductor devices.

FIG. 1 illustrates a conventional box-in-box overlay target 2 used with conventional image based overlay metrology methods. Target 2 is formed by producing an etched box 4 in first material layer on a substrate and another box 8 in a second material layer, or on the same layer. The target 2 is produced on the wafer off the chips, e.g., in the scribe lines between chips. The overlay target 2 is imaged to determine whether the second layer is properly aligned with the first layer. Other image based overlay targets, such as a bar-in-bar target, are produced and imaged in a similar fashion. Conventionally, high magnification imaging is used to measure image based overlay targets, such as target 2. Conventional imaging devices, unfortunately, suffer from disadvantages such as lack of sensitivity to vibration and cost. Moreover, conventional imaging devices suffer from a trade-off between depth-of-focus and optical resolution. Additionally, edge-detection algorithms used to analyze images for the purpose of extracting overlay error are inaccurate when the imaged target is inherently low-contrast or when the target suffers from asymmetries due to wafer processing. The existing method of image-based overlay is expected to reach its limit soon due to deviations from the actual device overlay error within the die. Image based overlay targets are outside the chip, e.g., in a scribe line and are larger scale than most current and future devices. Consequently, the overlay errors measured by image based overlay targets are not suitable to represent the true overlay error in the actual device area.

Another type of overlay measurement is performed using scatterometry, which relies on diffracting targets, such as diffraction gratings. Similar to image based overlay measurements, diffraction based overlay measurements require specialized off-chip targets. Diffraction based overlay measurements utilize the diffraction pattern produced by the target to determine overlay. The off-chip overlay targets use multiple overlying structures with different designed in offsets are used to determine the overlay error differentially, which requires a large amount of real estate on the wafer. Moreover, the off-chip location of the targets again may not accurately represent the overlay error in the actual device area.

Another type of asymmetry control is nano-imprint lithography for patterned media. Patterned media has been proposed to extend the hard disk drive magnetic recording density beyond 1 Tbit/inch$^2$ during the last couple of years. The implementation of patterned media requires the nano-imprint lithography (NIL, either thermal- or UV-NIL) to pattern the surface of the media. For NIL, the template is lowered and made contact with the pre-deposited disk substrate, and the region between the substrate and the topography of the imprint template is completely filled with imprint resist by the capillary action. When the template is released from the disk, the mirror image is replicated on the disk. Although symmetric resist profile is desired, tilted resist gratings are frequently seen on the disk after imprint. The non-expected tilting resist profile causes difficulties to the downstream processes or even makes them fail. Detect the tilting orientation and amount is becoming critical to improve the imprint process and ensure the success for patterned media. Metrology techniques used to conventionally measure an asymmetry such as tilt include cross-sectional scanning electron microscopy (SEM) imaging, but this method is destructive and the sample is destroyed after inspection. Atomic force microscopy (AFM) scans can provide partial information of grating profile as long as the AFM tip is able to reach the trench bottom. However, for small patterned media features on the order of a few tens of nanometers, current commercial AFM tips are too large to touch the bottom. Another downside factor of cross-sectional SEM and AFM is the slow throughput. Both methods are time consuming and hard to inspect the whole surface of the sample.

Optical techniques can be used to detect and quantify the asymmetric grating profile. Conventional optical scatterometry techniques, however, have the problem with asymmetric lines due to the lack of capability of distinguishing between left and right asymmetries.

Accordingly, there exists a need for improved asymmetry metrology techniques.

SUMMARY

Asymmetry metrology is performed by generating at least a portion of a Mueller matrix and analyzing the Mueller matrix, e.g., at least the off-diagonal elements of the Mueller matrix, to determine the value of the asymmetry, such as the offset between two overlying structures or the tilt of a diffraction grating or isolated structure. The Mueller matrix may be generated using, e.g., a spectroscopic or angle resolved ellipsometer that may include a rotating compensator. The Mueller matrix may be analyzed by fitting at least a portion of the elements to Mueller matrix elements calculated using a rigorous electromagnetic model of the sample or by fitting the combined anti-symmetric off-diagonal elements to a calibrated linear response. Using the Mueller matrix in asymmetry metrology advantageously permits the use of in-chip structures as the asymmetry target, thereby avoiding the need for special off-chip targets.

BRIEF DESCRIPTION OF THE DRAWINGS

FIG. 1 illustrates a conventional box-in-box overlay target used with conventional image based overlay metrology methods.

DETAILED DESCRIPTION

Figure 2:
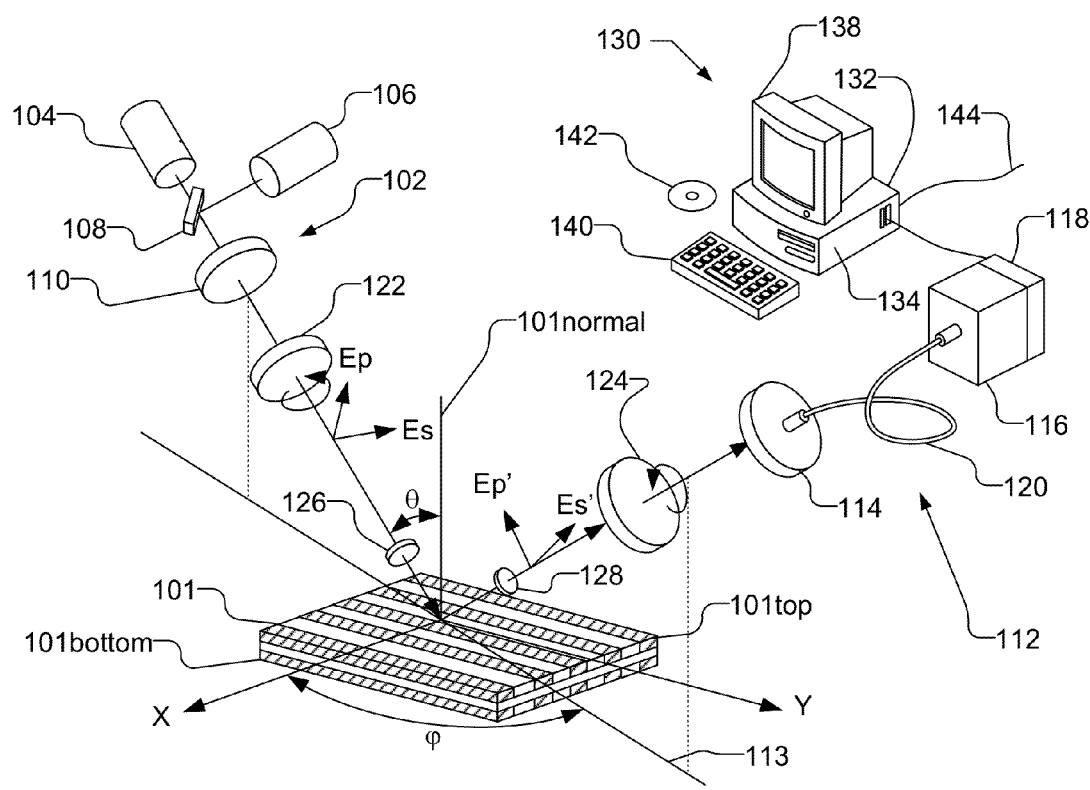
FIG. 2 illustrates an ellipsometer that may be used to perform asymmetry metrology based on at least a portion of the Mueller matrix.

FIG. 2 illustrates an ellipsometer 100 that may be used to perform an asymmetry measurement of a structure on a sample based on at least a portion of the Mueller matrix. The sample 101 illustrated in FIG. 2 includes two overlaying diffraction patterns 101top and 101bottom, where the asymmetry measurement may be a measurement of the overlay error in the overlaying diffraction patterns 101top and 101bottom. Ellipsometer 100, however, may be used with different samples, and may make different asymmetry measurements.

Ellipsometer 100 is a rotating compensator ellipsometer 100 that performs a diffraction based measurement on the sample 101. The ellipsometer 100 includes a polarization state generator (PSG) 102 and a polarization state detector (PSD) 112. The PSG 102 produces light having a known polarization state and is illustrated as including two broadband light sources 104 and 106, e.g., a Xenon Arc lamp and a Deuterium lamp, respectively, to produce light with a range of 200-100 nm. A beam splitter 108 combine the light from the light sources 104, 106 and a polarizer 110 produces the known polarization state. It should be understood that additional, different, or fewer light sources may be used if desired. Moreover, if desired, ellipsometer 100 may be monochromatic, with a variable angle of incidence to provide angle resolved measurements.

The PSD 112 includes a polarizing element, referred to as an analyzer 114, a spectrometer 116 and a detector 118, which may be, e.g., a cooled CCD array. The analyzer 114 is illustrated as being coupled to the spectrometer 116 and detector 118 via a fiber optic cable 120. It should be understood that other arrangements are possible, such as directly illuminating the spectrometer 116 from the analyzer 114 without the fiber optic cable 120.

The ellipsometer 100 is illustrated with two rotating compensators 122 and 124 between the PSG 102 and PSD 112. If desired, the ellipsometer 100 may use a single rotating compensator 122 or 124, e.g., between the PSG 102 and the sample 101 or between the sample 101 and the PSD 112, respectively. The ellipsometer 100 may further include focusing elements 126 and 128 before and after the sample 101, as illustrated in FIG. 2. The focusing elements may be, e.g., refractive or reflective lenses.

The ellipsometer 100 obliquely illuminates the sample 101, e.g., at a non-zero value of θ with respect to surface normal 126. For example, the ellipsometer 100 may illuminate the sample 101 at an angle between 50° to 85°, for example at 65°, but other angles may be used if desired. As discussed above, if monochromatic light is used, the angle of incidence may be varied to derive an angle resolved measurement. The plane of incidence 113 is at an angle φ with respect to the direction of periodicity of the diffraction pattern on the sample 101, identified in FIG. 2 as along axis X. For example, the angle φ may be 0°, 90°, or anywhere in between, e.g., 45°. By way of example, the ellipsometer may be a M2000 ellipsometer produced by JA Woollam Co., Inc.

As illustrated in FIG. 2, the detector 118 is coupled to a computer 130, which includes a processor 132 with memory 134, as well as a user interface including e.g., a display 138 and input devices 140. A computer-usable medium 142 having computer-readable program code embodied may be used by the computer 130 for causing the processor to control the device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 142, which may be any device or medium that can store code and/or data for use by a computer system such as processor 132. The computer-usable medium 142 may be, but is not limited to, magnetic and optical storage devices such as disk drives, magnetic tape, compact discs, and DVDs (digital versatile discs or digital video discs). A communication port 144 may also be used to receive instructions that are used to program the computer 130 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Ellipsometry typically examines the changes in the p- and s-components of light caused by reflection or transmission from a sample. For example, light having a known polarization state from the PSG 102 is produced and incident on the sample and the resulting change in the polarization state is measured by the PSD 112. The change in polarization state is typically written as follows:

$$R_p = \frac{E'_p}{E_p}; \quad R_s = \frac{E'_s}{E_s}. \qquad \text{Eq. 1}$$

In equation 1, $E_p$ and $E_s$ are the electrical vectors for the respective parallel and perpendicular components of the elliptically polarized incident light and $E'_p$ and $E'_s$ are the parallel and perpendicular components, respectively, of the elliptically polarized reflected light, and $R_p$ and $R_s$ are the reflection coefficients of the sample for the parallel and perpendicular components of light. The ellipsometric sample parameters $\psi$ and $\Delta$ are then conventionally determined as follows:

$$\frac{R_p}{R_s} = \tan\psi e^{i\Delta}. \qquad \text{Eq. 2}$$

Figure 3A:
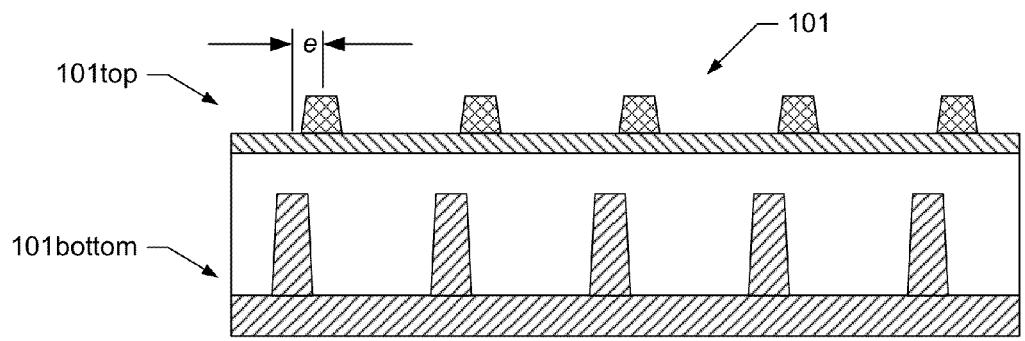
FIGS. 3A, 3B, 3C, 3D, 3E, 3F and 3G illustrate samples that may have asymmetries.

Conventionally, a diffraction based measurement of a sample is based on the spectral response of the scattered light to the structure of the sample. The response is typically measured ellipsometrically by monitoring the change in $\psi$ (the ratio of $R_p/R_s$) and $\Delta$ (phase difference between $R_p$ and $R_s$). To evaluate this measured change, a model of the sample is produced and ellipsometric data is calculated from the model. FIG. 3A, by way of example, illustrates a cross-sectional view of a sample 101 in the form of an overlay target with overlying diffraction patterns 101top and 101bottom and an overlay error e. As illustrated in FIG. 3A, one or more layers may be between the overlying diffraction patterns 101top and 101bottom or alternatively, the patterns may be on the same level, as illustrated in FIGS. 3F and 3G where the bottom layer 101bottom is the first layer deposited and the top layer 101top is the subsequent deposited layer, which is deposited on the same level as bottom layer 101bottom. FIG. 3F illustrates a perspective view of a structure in which the first deposited layer 101bottom is e.g., etched into silicon with surrounding space filled with silicon dioxide, then in a second etch step another structure is etched in the bottom layer 101bottom and material deposited to form top layer 101top, where an overlay error exists between the first and second layers 101bottom and 101top. FIG. 3G illustrates a double patterned sample 101 where the grating has lines 101bottom and 101top on the same level, where an overlay error e is evident. With a diffraction based overlay target, such as sample 101 illustrated in FIGS. 3A, 3F, and 3G, a model of the overlying diffraction patterns 101top and 101bottom are produced with an overlay error, along with other parameters, such as height, CD, and sidewall angle. The measured ellipsometric data is compared to the calculated ellipsometric data to determine if there is a good fit. If the measured and calculated ellipsometric data have a good fit, then the model of the sample 101 is considered to be an accurate representation of the sample including the overlay error. On the other hand, if a good fit is not achieved, a different model of the sample 101, e.g., with a different overlay error and/or other parameters, along with corresponding calculated ellipsometric data is obtained, e.g., either from a library or in a real-time calculation, and compared with the measured ellipsometric data. This process is repeated until a good fit is achieved.

Another diffraction based overlay metrology method uses a plurality of targets, each with a slightly different designed in offset. A differential analysis can then be performed using the measured results from the plurality of targets, thereby avoiding the need to model the target and fit the measurement.

Unfortunately, both conventional techniques for diffraction based overlay metrology requires a specially designed target, which must be located outside of the die area, e.g., in a scribe line. Moreover, the target designs typically are two-orders of magnitude larger in line and space dimensions than the in-die devices. Consequently, the measured overlay from the specially designed remote targets may not accurately represent the overlay error within the die.

Figure 3B:
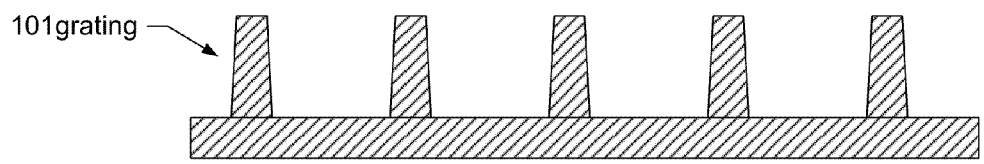
Figure 3C:
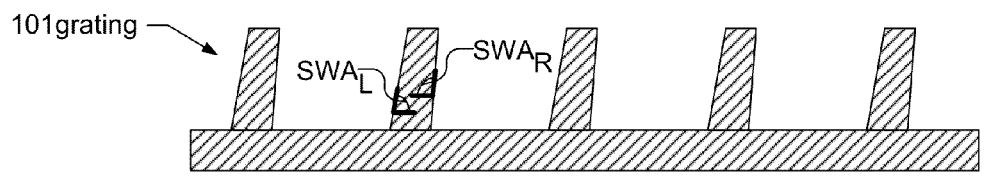
Figure 3D:
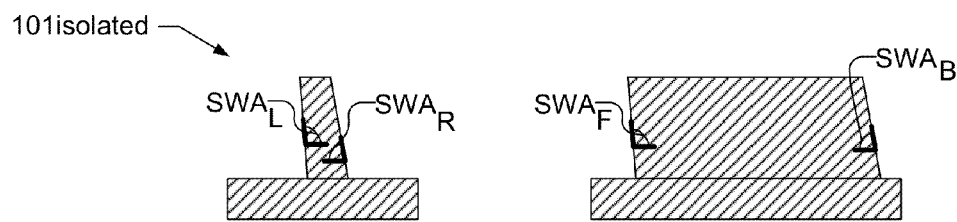
Figure 3E:
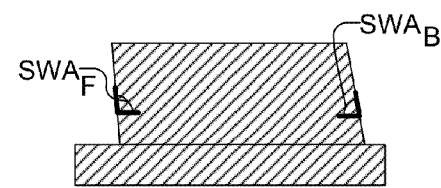
Figure 3F:
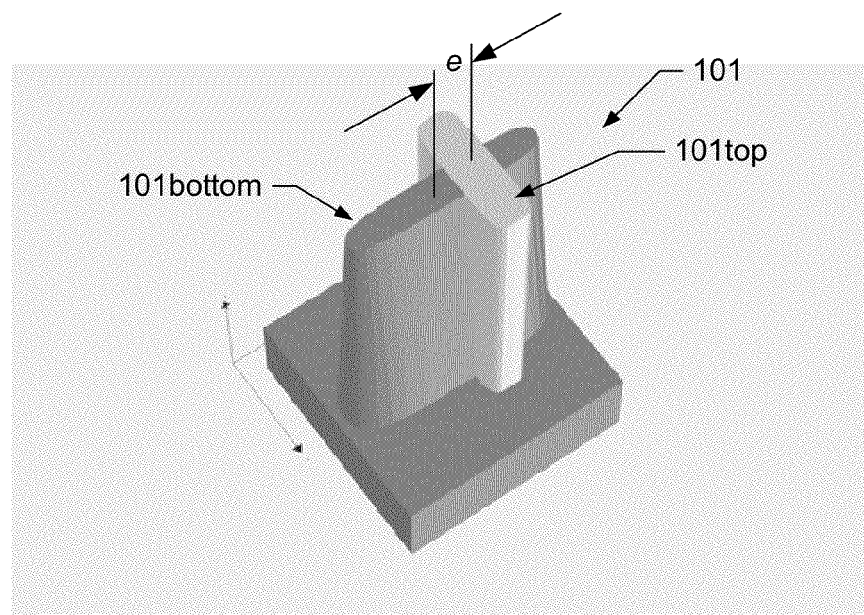
Figure 3G:
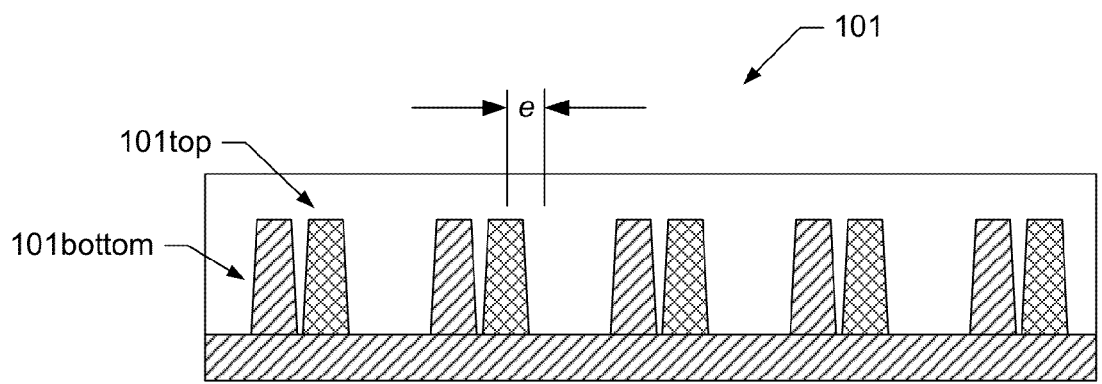

Other type of asymmetry measurement that may be performed by ellipsometer 100 is illustrated in FIGS. 3B and 3C. FIGS. 3B and 3C illustrate a one-dimensional grating structure $101_{grating}$, which may be found in an microelectronic device or in a hard disk patterned media, e.g., in the form of patterned tracks. By way of example, the structure shown in FIGS. 3B and 3C is typical for an imprint hard disk at the litho patterning step, e.g., for a 350 k TPI disk, which may have a pitch of 73 nm, a critical dimension (CD) of 48 nm and a height of 60 nm. Of course, other parameters of the pitch, CD, or height are possible. In normal processing, symmetric gratings are desired as shown in FIG. 3B. When the process is not operated at optimum conditions, the gratings may be tilted, as illustrated in FIG. 3B. FIG. 3B illustrates the grating $100_{grating}$ tilted to the right, e.g., where the $SWA_L$ is less than the $SWA_R$. Tilt may be quantified as $\delta_{SWA} = SWA_R - SWA_L$. Of course, the grating $100_{grating}$ may tilt to the left as well. Moreover, the grating structure may tilt to left at some locations on the disk and tilt to the right at other locations. FIG. 3D illustrates an asymmetrical isolated structure $101_{isolated}$, e.g., with a left tilt, which ellipsometer 100 may be used to measure the asymmetry. Moreover, asymmetry of the structure may be detected in more than one direction, e.g., measurable asymmetry may exist in both the x and y directions, or non-orthogonal directions. For example, FIG. 3E illustrates a side view of structure $101_{grating}$ where the front side wall angle $SWA_F$ and back side wall angle $SWA_B$ may be measured along with the right and left side wall angles. For example, structure $101_{grating}$ in FIG. 3E may be in a bit pattern media, where the measurable asymmetry of islands may be present to the inside or outside of the disk while another measurable asymmetry may be present at the leading or trailing edge of the island.

Using at least several specific elements from the Mueller matrix produced by ellipsometer 100, the asymmetry of a structure, including overlay error or tilt, may be measured. The use of the Mueller matrix allows measurement of asymmetry without using dedicated targets. Accordingly, overlay error, for example, may be measured using in die structures without using dedicated overlay targets. The use of in die devices to measure asymmetry such as overlay error, a significant savings in real estate on the sample is possible because no special targets are needed, e.g., in the scribe line. Consequently, other types of targets may be placed in the scribe line or more dies may be produced on a wafer. Much more sophisticated sampling scheme is also possible, including direct in-die measurement, whereas metrology on the scribe lines is limited to a per die sampling rate.

The Mueller matrix M is a 4×4 matrix that describes the sample being measured and is related to the Jones matrix J as follows:

$$M = TJ \otimes J^* T^{-1} \qquad \text{Eq. 3}$$

The Jones matrix describes the sample-light interaction as follows:

$$J = \begin{pmatrix} r_{ss} & r_{sp} \\ r_{ps} & r_{pp} \end{pmatrix} \quad \text{Eq. 4}$$

$$\begin{pmatrix} E'_s \\ E'_p \end{pmatrix} = \begin{pmatrix} r_{ss} & r_{sp} \\ r_{ps} & r_{pp} \end{pmatrix} \begin{pmatrix} E_s \\ E_p \end{pmatrix}. \quad \text{Eq. 5}$$

The Jones matrix depends on the angle of incidence, azimuth, wavelength as well as structural details of the sample. The diagonal elements describe the complex reflectance (amplitude & phase) for polarization orthogonal ($r_{ss}$) and parallel ($r_{pp}$) to the plane incidence defined by the illumination and collection arms. The off-diagonal terms $r_{sp}$ and $r_{pp}$ are related to polarization conversion between s and p polarization states in the presence of sample anisotropy. The Jones matrix J Not all of the elements of the Mueller matrix M are required in order to accurately measure asymmetry. For example, using one rotating compensator, e.g., compensator 122, the first three rows of the Mueller matrix M can be obtained, which can be used to determine an asymmetry. Additionally, if desired, an ellipsometer with a rotating polarizer 110 and analyzer 114 and no rotating compensators can be used to experimentally determine the nine elements in the first three rows and first three columns of the Mueller matrix M, which may be used to adequately determine an asymmetry. In the above described ellipsometry configurations, the obtained signal at the detector is a time dependent intensity. From the time dependent intensity signal and Fourier analysis it is possible to obtain a system of equations that are solved for either a partial or a full set of Mueller elements. With the use of ellipsometer 100 using both rotating compensators 122 and 124, all of the elements of the Mueller matrix M can be obtained experimentally as follows.

$$M_{sample} = \begin{bmatrix} \frac{(r^*_{ss}r_{ss} + r^*_{pp}r_{pp} + r^*_{sp}r_{sp} + r^*_{ps}r_{ps})}{2} & \frac{(-r^*_{ss}r_{ss} + r^*_{pp}r_{pp} - r^*_{sp}r_{sp} + r^*_{ps}r_{ps})}{2} & \text{Re}(r^*_{pp}r_{ps} + r^*_{sp}r_{ss}) & -\text{Im}(r^*_{pp}r_{ps} + r^*_{sp}r_{ss}) \\ \frac{(-r^*_{ss}r_{ss} + r^*_{pp}r_{pp} + r^*_{sp}r_{sp} - r^*_{ps}r_{ps})}{2} & \frac{(r^*_{ss}r_{ss} + r^*_{pp}r_{pp} - r^*_{sp}r_{sp} - r^*_{ps}r_{ps})}{2} & \text{Re}(r^*_{pp}r_{ps} - r^*_{sp}r_{ss}) & \text{Im}(-r^*_{pp}r_{ps} + r^*_{sp}r_{ss}) \\ \text{Re}(r^*_{pp}r_{sp} + r^*_{ps}r_{ss}) & \text{Re}(r^*_{pp}r_{sp} - r^*_{ps}r_{ss}) & \text{Re}(r^*_{pp}r_{ss} + r^*_{sp}r_{ps}) & \text{Im}(-r^*_{pp}r_{ss} + r^*_{sp}r_{ps}) \\ \text{Im}(r^*_{pp}r_{sp} + r^*_{ps}r_{ss}) & \text{Im}(r^*_{pp}r_{sp} - r^*_{ps}r_{ss}) & \text{Im}(r^*_{pp}r_{ss} + r^*_{sp}r_{ps}) & \text{Re}(r^*_{pp}r_{ss} - r^*_{sp}r_{ps}) \end{bmatrix} \quad \text{Eq. 9}$$

elements, however, are not easily obtained experimentally. The elements of the 4×4 Mueller matrix M, however, can be derived experimentally.

The matrix T in equation 3 is used to construct the 4×4 Mueller matrix from the Jones matrix and is given by:

$$T = \begin{pmatrix} 1 & 0 & 0 & 1 \\ 1 & 0 & 0 & -1 \\ 0 & 1 & 1 & 0 \\ 0 & i & -i & 0 \end{pmatrix} \quad \text{Eq. 6}$$

The Mueller matrix is measured by the ellipsometer 100, and the Jones matrix is calculated from first principles for a given sample. So to compare the theoretical calculation to the experimental data one needs to convert the Jones matrix to Mueller matrix.

The Mueller matrix M may be written in the Stokes formalism as follows:

$$\begin{pmatrix} s_0 \\ s_1 \\ s_2 \\ s_3 \end{pmatrix}^{out} = \begin{pmatrix} m_{11} & m_{12} & m_{13} & m_{14} \\ m_{21} & m_{22} & m_{23} & m_{24} \\ m_{31} & m_{32} & m_{33} & m_{34} \\ m_{41} & m_{42} & m_{43} & m_{44} \end{pmatrix} \begin{pmatrix} s_0 \\ s_1 \\ s_2 \\ s_3 \end{pmatrix}^{in}. \quad \text{Eq. 7}$$

The Stokes vector S is described as follows:

$$S = \begin{pmatrix} s_0 \\ s_1 \\ s_2 \\ s_3 \end{pmatrix} = \begin{pmatrix} |E_s|^2 + |E_p|^2 \\ |E_s|^2 - |E_p|^2 \\ 2\text{Re}(E_s E_p^*) \\ 2\text{Re}(E_s E_p^*) \end{pmatrix} = \begin{pmatrix} \text{total power } P \\ P_{0°} - P_{90°} \\ P_{45°} - P_{45°} \\ P_{RHC} - P_{LHC} \end{pmatrix}. \quad \text{Eq. 8}$$

The Mueller matrix elements are sensitive to the profile details of the structures as well as any asymmetries present, e.g. any misalignment between objects at different levels in the structure or tilting of the structure. The Mueller matrix can be used for the detection of asymmetries due to the fact that the Jones cross-reflection coefficients, i.e., and $r_{ps}$ and $r_{sp}$ in equation 5 are anti-symmetric for symmetric structures. In other words, for symmetric gratings the specular, or 0th order, cross reflection coefficients in the conical mount, are anti-symmetric, i.e. $r_{sp} = -r_{ps}$. When the structural symmetry is broken, this relationship is violated and $r_{sp} \neq -r_{ps}$, which can be exploited for asymmetry measurement including misalignment control, overlay metrology, or tilt metrology. As discussed above, the cross-reflection coefficients of the Jones matrix are not easily obtained experimentally. However, the anti-symmetric property of certain elements in the Jones matrix for symmetric structures translates to similar relations for Mueller matrix elements, which, thus, can also be exploited for asymmetry metrology.

By way of example, Mueller matrix elements $M_{13}$ and $M_{31}$ as well as elements $M_{23}$ and $M_{32}$ are anti-symmetric for symmetric structures. This property of the Jones matrix for symmetric structures mathematically translates for the Mueller elements as follows:

$$M_{13} + M_{31} = 0$$

$$M_{23} + M_{32} = 0 \quad \text{Eq. 10}$$

Moreover, in the regime of small overlay errors there is a linear relationship in the anti-symmetry of the elements and overlay error e as follows:

$$M_{13} + M_{31} = C_1 e$$

$$M_{23} + M_{32} = C_2 e \quad \text{Eq. 11}$$

where $C_1$ and $C_2$ are constants. Thus, by analyzing at least the cross reflection coefficients of the Muller matrix, including $M_{13}$, $M_{31}$ and $M_{23}$, $M_{32}$ the alignment or overlay error of the structure can be evaluated. Further, it has been determined that off-diagonal elements, $M_{13}$, $M_{14}$, $M_{23}$, $M_{24}$, $M_{31}$, and $M32$ are generally sensitive to asymmetry. For example, these off-diagonal elements are sensitive to the sign of the tilt parameter $\delta_{SWA}$ as well as the amplitude of the tiling and can therefore be used to not only distinguish between left-tilting and right-tilting, but provide a measurement of the amount of tilting.

Figure 4:
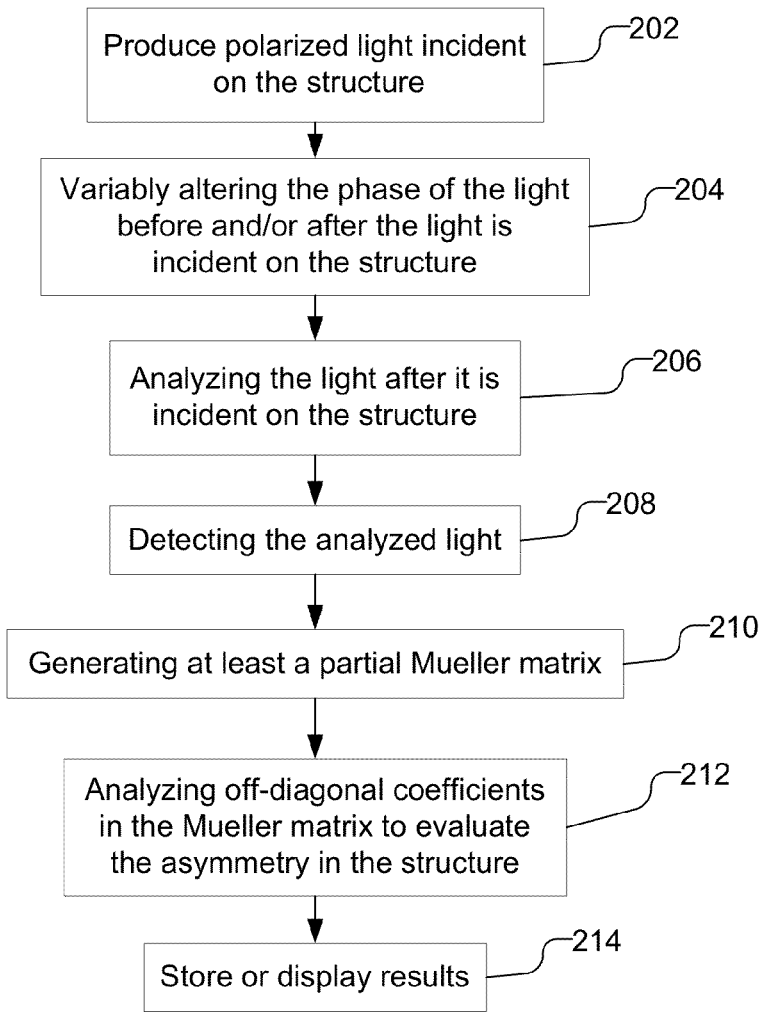
FIG. 4 is a flow chart illustrating a method of using the Mueller matrix to evaluate the asymmetry of a sample.
Figure 5A:
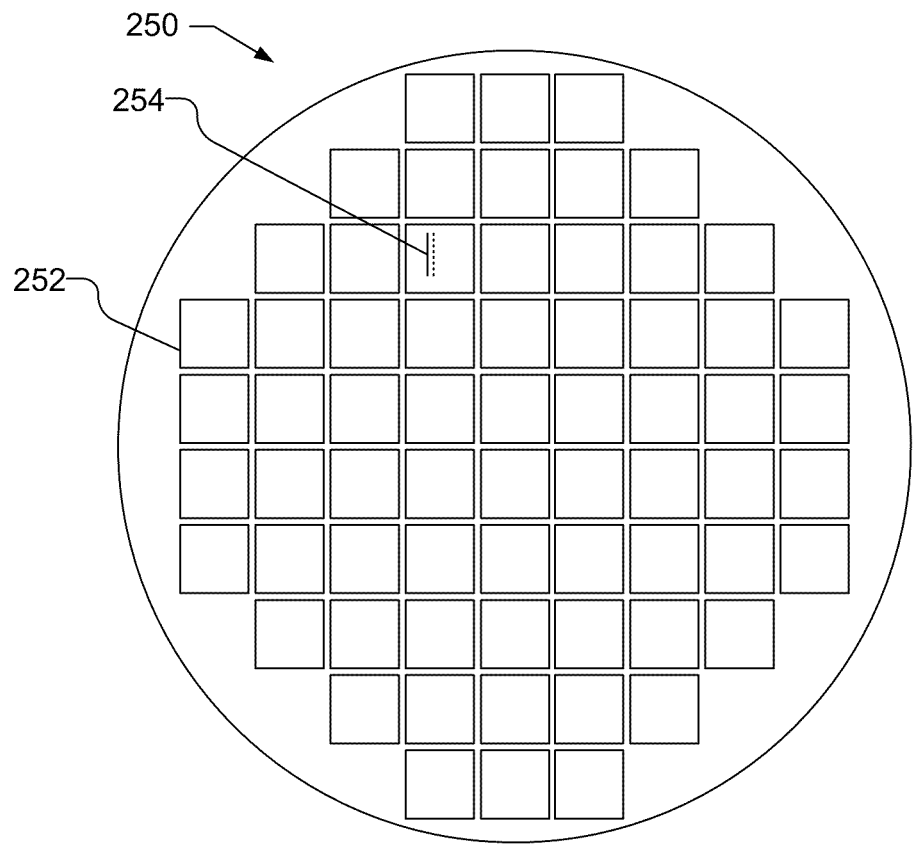
FIG. 5A illustrates a wafer that includes a plurality of dies with an in-die structure that is may be used as an overlay target.
Figure 5B:
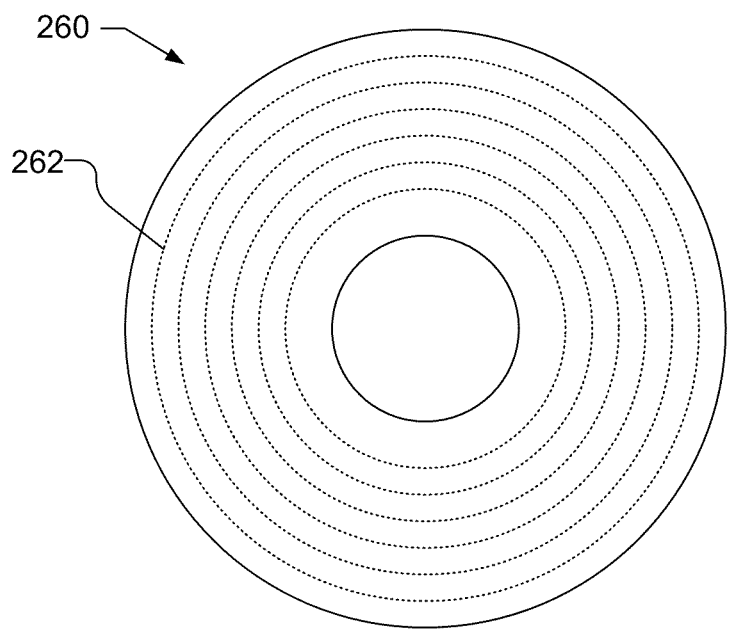
FIG. 5B illustrates an imprint hard disk that includes a plurality of grating lines.

FIG. 4 is a flow chart illustrating a method of using the Mueller matrix to evaluate the asymmetry of a sample. Polarized light is produced and incident on the structure on the sample that is to be measured (202). The structure may be an overlay target including overlying diffraction gratings, as illustrated in FIG. 3A or may be a single grating structure, such as that shown in FIGS. 3B and 3C or may be an isolated structure as illustrated in FIG. 3D. The structure need not be a dedicated target, such as a dedicated overlay target, but instead may be device structures within the active area of the sample, e.g., within the die. For example, FIG. 5A illustrates a wafer 250 that includes a plurality of dies 252. Overlaying structures 254, illustrated as a top structure (solid line) and a bottom structure (dotted line), are located within a die. Each die 252 or a plurality of dies 252 may be measured. Moreover, a plurality of locations within the die 252 may be measured. FIG. 5B illustrates an imprint hard disk 260 that includes a plurality of grating lines 262, all within the active area of the disk 260.

The phase of the light may be variably altered using one or both of the rotating compensators 122 and 124 (204), which is useful for determining the first three rows or all four rows of the Mueller matrix. A sufficient number of elements of the Mueller matrix may be determined without the use of rotating compensators, and thus, step 204 may be skipped if desired. After the light is incident on and interacts with the overlying structures, the light is analyzed using analyzer 114 to polarize the light with a known polarization state (206). The analyzed light is detected, e.g., by spectrometer 116 and detector 118 (208). Using the detected light, at least a partial Mueller matrix is generated (210). At least the off-diagonal coefficients of the Mueller matrix, including the cross reflection coefficients, e.g., $M_{13}$, $M_{31}$ and $M_{23}$, $M_{32}$, are analyzed to evaluate the asymmetry of the structure (212), such as alignment, overlay error, or tilting, and the result is stored or displayed (214). The off-diagonal coefficients of the Muller matrix may be analyzed by fitting the measured off-diagonal coefficients of the Muller matrix to modeled off-diagonal coefficients of the Muller matrix. If desired, all of the Mueller matrix coefficients, i.e., not only the off-diagonal coefficients may be analyzed. A real-time analysis may be used in which the model parameters are adjusted through non-linear regression or, alternatively, a library may be used. Alternatively, the off-diagonal coefficients of the Muller matrix may be analyzed using a calibrated linear response of measured or modeled off-diagonal coefficients of the Muller matrix.

Figure 6:
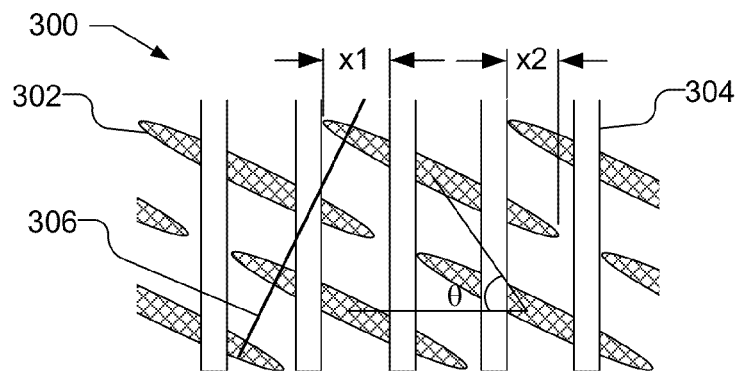
FIG. 6 illustrates a top plan view of a portion of an in-chip structure that may be used an overlay target.

One form of asymmetry that may be measured is an alignment or overlay error. By way of example, FIG. 6 illustrates a top plan view of a portion of an in-chip structure 300 that can be measured for overlay error. The structure 300 is a portion of a DRAM device and includes overlying structures including a shallow trench isolation (STI) array of islands 302 at a bottom layer and photo-resist lines 304 at the top layer, with several thin film layers in between. As can be seen, the silicon islands 302 are arranged in a non-orthogonal lattice and are rotated with respect to the horizontal axis. The space surrounding the silicon islands 302 is filled with silicon dioxide. The structure 300 may include materials between the islands 302 and the resist lines 304, such as a silicon oxi-nitride layer and anti-reflective coating layer. The resist lines 304 are formed over the top of the STI structure. When there is an overlay error in the structure 300, the resist lines 304 are shifted relative to the islands 302, where the overlay error is for this structure is defined as $\delta x=(x1-x2)/2$. In the final etched structure, an overlay error makes the two ends of the elongated STI island 302 non-equal, therefore breaking the symmetry of the structure. Thus, the on-chip device structure 300 may be used as an overlay target by exploiting the breaking of symmetry using the Mueller matrix metrology. It should be understood that the Muller matrix metrology may be used with other on-chip devices besides the particular DRAM structure illustrated, including flash memory and logic structures, as well as off-chip diffraction based overlay targets, such as that illustrated in FIG. 3A.

For the type of complex three-dimensional structure shown in FIG. 6, it is possible to take ellipsometry measurements along several high symmetry azimuth angles, e.g., angle $\phi$ in FIG. 2. The azimuth angle $\phi$ is dependent on the structure being measured and for complex structures, a sensitivity study in which several high symmetry angles are measured and compared may be performed to determine the best sensitivity. For the structure shown in FIG. 6, it has been determined that the best sensitivity is achieved with an azimuth angle that is orthogonal to the long axis of the STI islands 302 as illustrated by line 306 in FIG. 6. A description of the sensitivity study for azimuth angle optimization may be found at P. Vagos, J. Hu, Z. Liu & S. Rabello, "Uncertainty and Sensitivity Analysis and its application in OCD measurements", Proc. of SPIE 7272, 72721N-72721N-9 (2009), which incorporated herein by reference.

Figure 7:
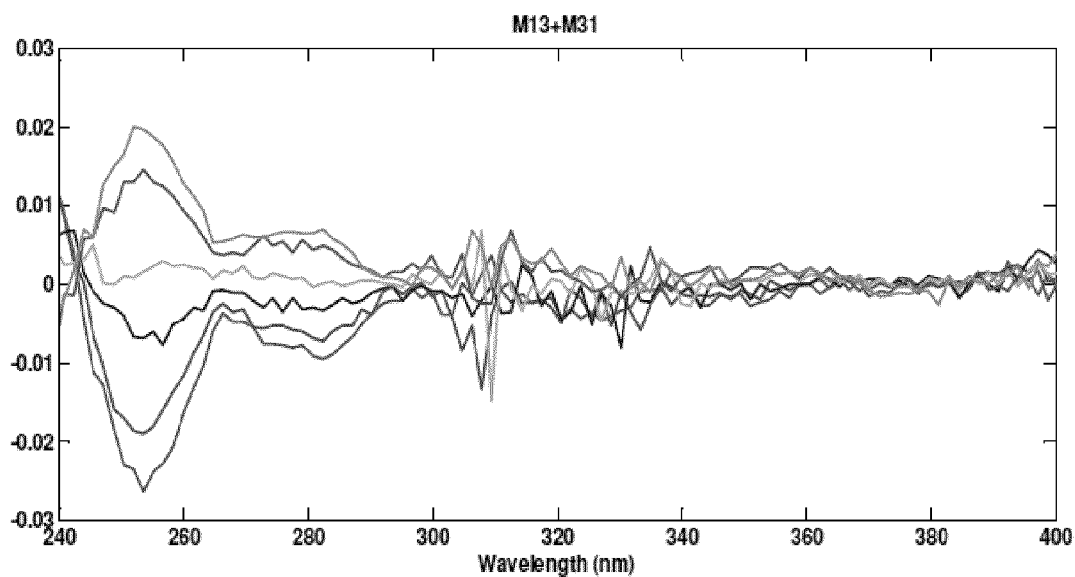
FIG. 7 illustrates the spectral response for combination of two Mueller matrix elements to different overlay shifts.
Figure 8:
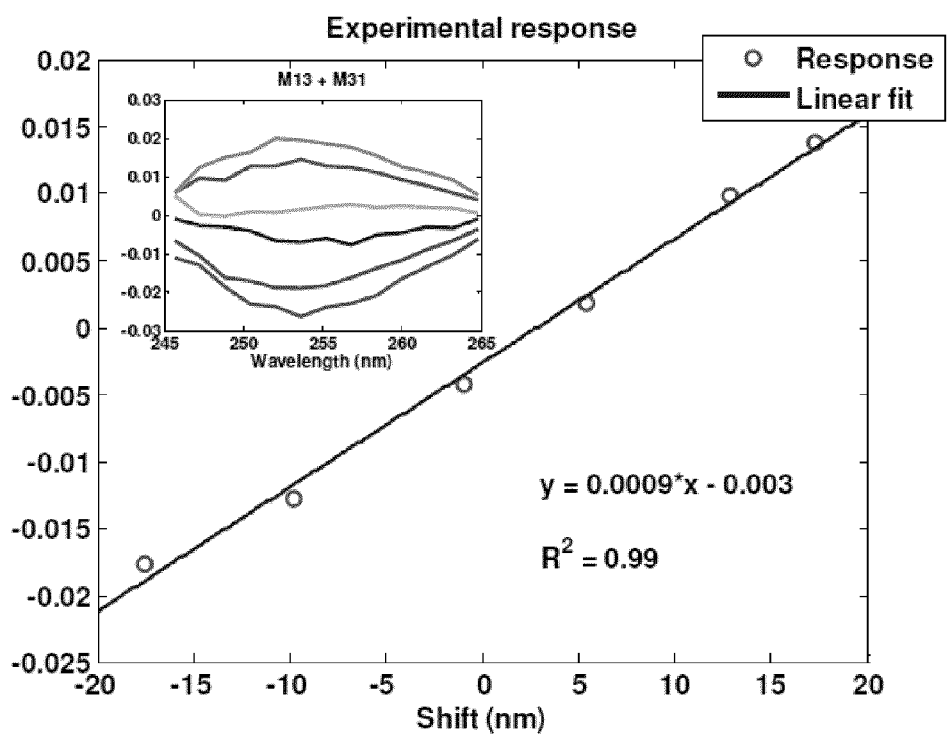
FIG. 8 illustrates the spectral response averaged over the UV range for the overlay shift.

FIG. 7 illustrates the spectral response for combination of two off-diagonal, cross-reflection Mueller matrix elements $(M_{13}+M_{31})$ to different overlay shifts between top and bottom layers, ranging from +15 nm to −15 nm, in structures similar to structure 300 shown in FIG. 6. The Muller matrix is adimensional and is bound to the [−1,1] interval. The structures used to produces the experimental response were produced using varying intentional overlay displacements for the structure across the diameter of a 300 mm silicon wafer. Each curve in FIG. 7 corresponds to a different overlay shift in the ±15 nm range. From equation 11, the amplitude of $M_{13}+M_{31}$ directly corresponds to the asymmetry induced by the overlay error in the structures. As can be seen, the spectra have well formed oscillations across the wavelength range, with the highest amplitude oscillations between 245-265 nm. FIG. 8 illustrates the spectral response averaged over the 245-265 nm wavelength range for the overlay shift. As can be seen, the mean response is nearly linear within the ±15 nm range of overlay error.

Figure 9:
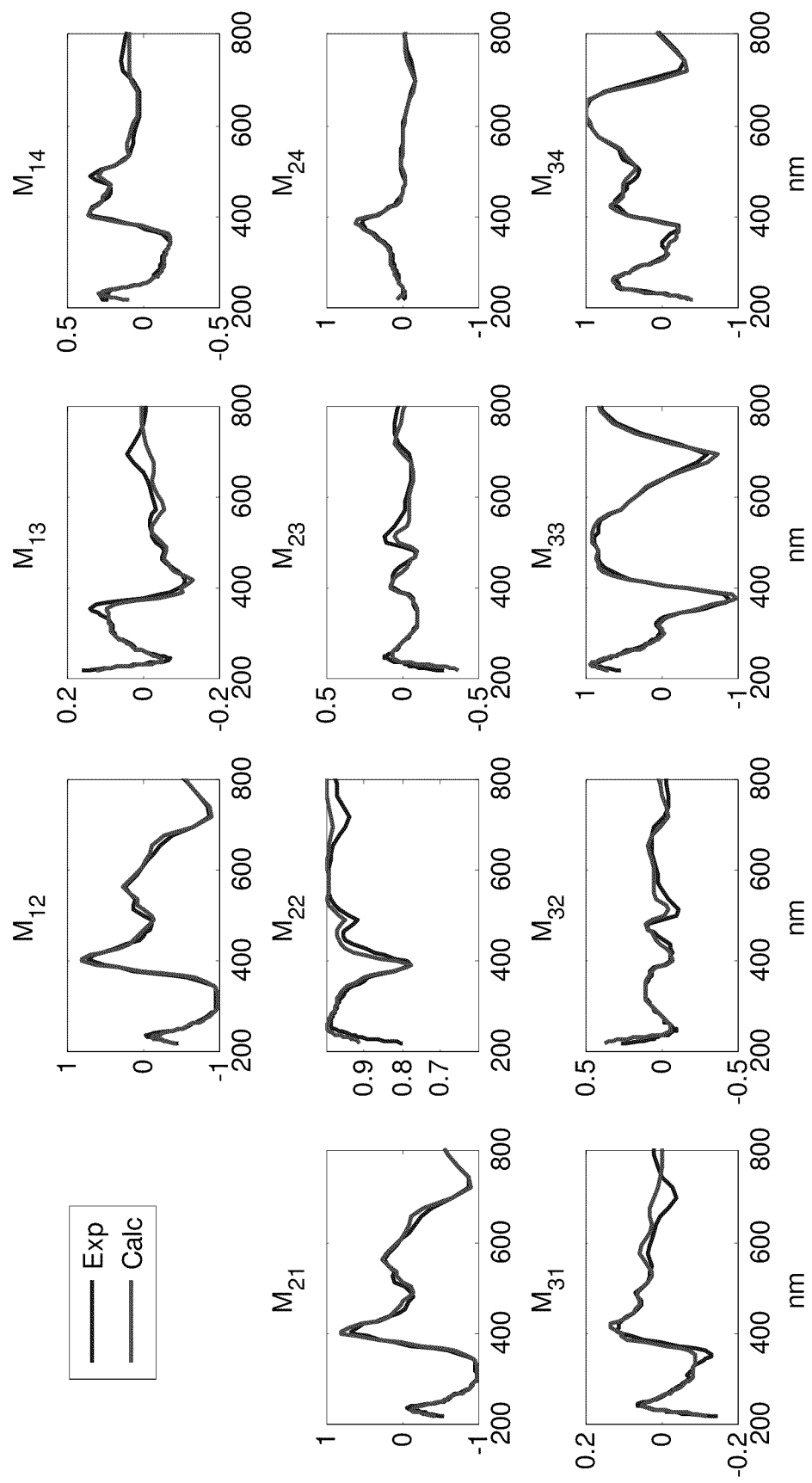
FIG. 9 illustrates a set of measured and fit spectra for 11 Mueller matrix elements.

FIG. 9 illustrates a set of measured and fit spectra for 11 Mueller matrix elements, i.e., the first three rows, measured by a spectroscopic ellipsometer 100 using a single rotating compensator 122 for a structure similar to structure 300 shown in FIG. 6. The spectra illustrated in FIG. 9 are wavelength resolved as a spectroscopic ellipsometer is used. If desired, an angle resolved measurement may alternatively be used. The Mueller matrix element $M_{11}$ is defined as 1 and is therefore not shown. As can be seen, the spectra for Mueller matrix elements $M_{13}$ and $M_{31}$ are nearly anti-symmetric, as are the spectra for Mueller matrix elements $M_{23}$ and $M_{32}$. The change induced by the overlay shift in the sample structure is relatively small compared to the amplitude in the spectra for the cross reflection coefficients of the Muller matrix, e.g., $M_{13}$, $M_{31}$ and $M_{23}$, $M_{32}$.

Figure 10:
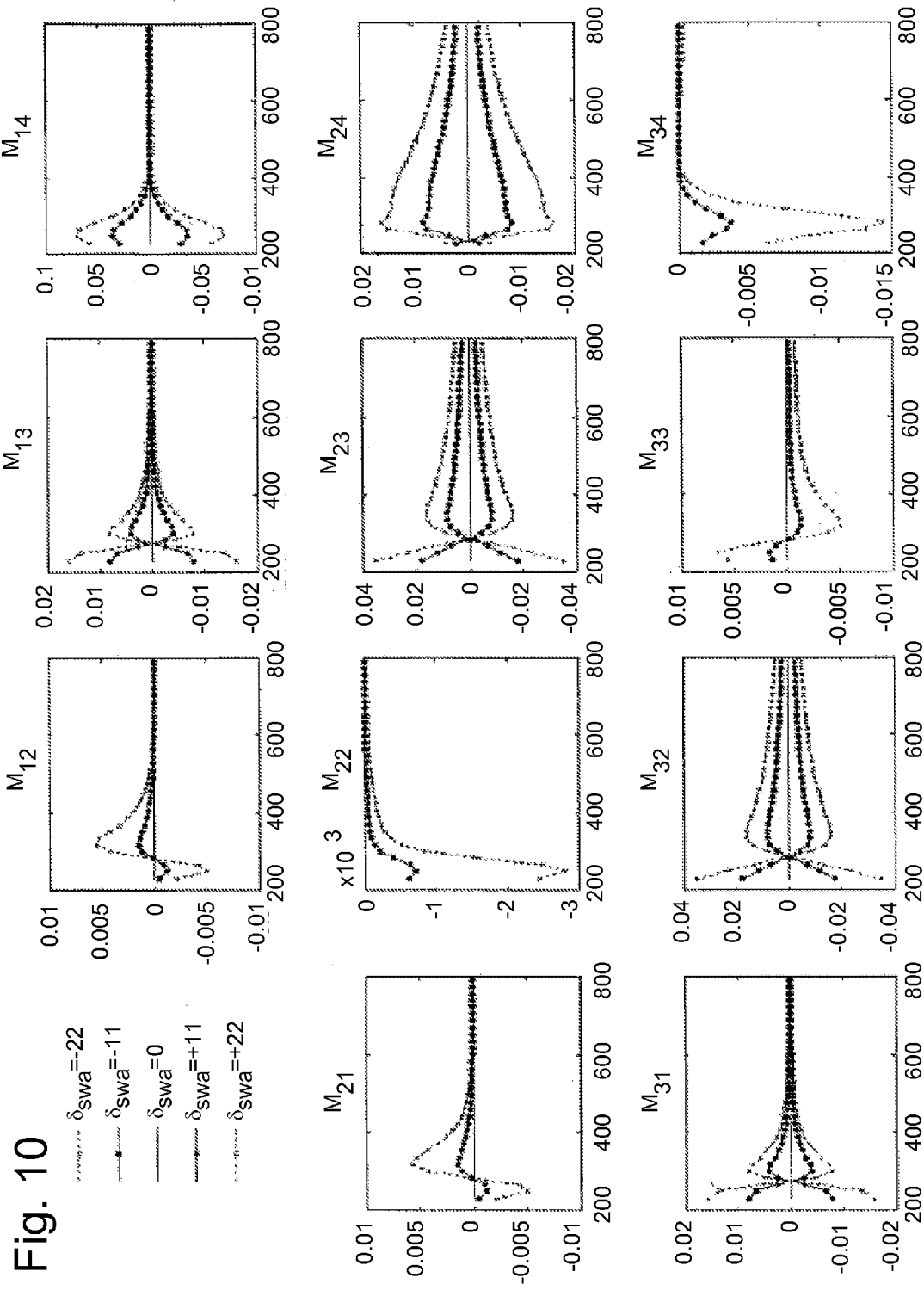
FIG. 10 illustrates the Mueller matrix elements for simulations of different tilt values of a sample.

Another form of asymmetry that may be measured is the tilting of a structure, as illustrated in FIGS. 3B, 3C, and 3D, which may be found, e.g., on an imprint hard disk, such as disk 260 shown in FIG. 5B. For the ellipsometry measurement, an angle of incidence of 65° from normal may be used with the plane of incidence at an azimuth angle of 90°, also referred as conical mount because all diffracted orders of reflected beams are on the surface of a cone about the direction of the grating lines. FIG. 10 illustrates the Mueller matrix elements for simulations performed using NanoDiffract™ software with an RCWA algorithm. The structure is similar to that shown in FIG. 3B with five different $\delta_{SWA}$ values, −22°, −11°, 0°, +11° and +22°. The CDs of the gratings at any given height do not change for the structures in the simulation, i.e., the gratings are only pushed toward left or right but the volume is kept constant. Data are shown as the deviation from the symmetric grating, i.e., $\delta_{SWA}=0°$. As can be seen in FIG. 10, for the Mueller matrix elements m12, m21, m22, m33 and m34, a $\delta_{SWA}$ with the same amplitude but opposite sign have an identical optical response; therefore, only three curves can be seen and no identification of the direction of the tilt can be obtained. The remaining Mueller matrix off-diagonal elements, $M_{13}$, $M_{14}$, $M_{23}$, $M_{24}$, $M_{31}$, and $M_{32}$, however, are not only sensitive to the sign of tilt $\delta_{SWA}$, and thus can distinguish left-tilting from right-tilting, but is also sensitive to the amplitude of the tilt.

Figure 11:
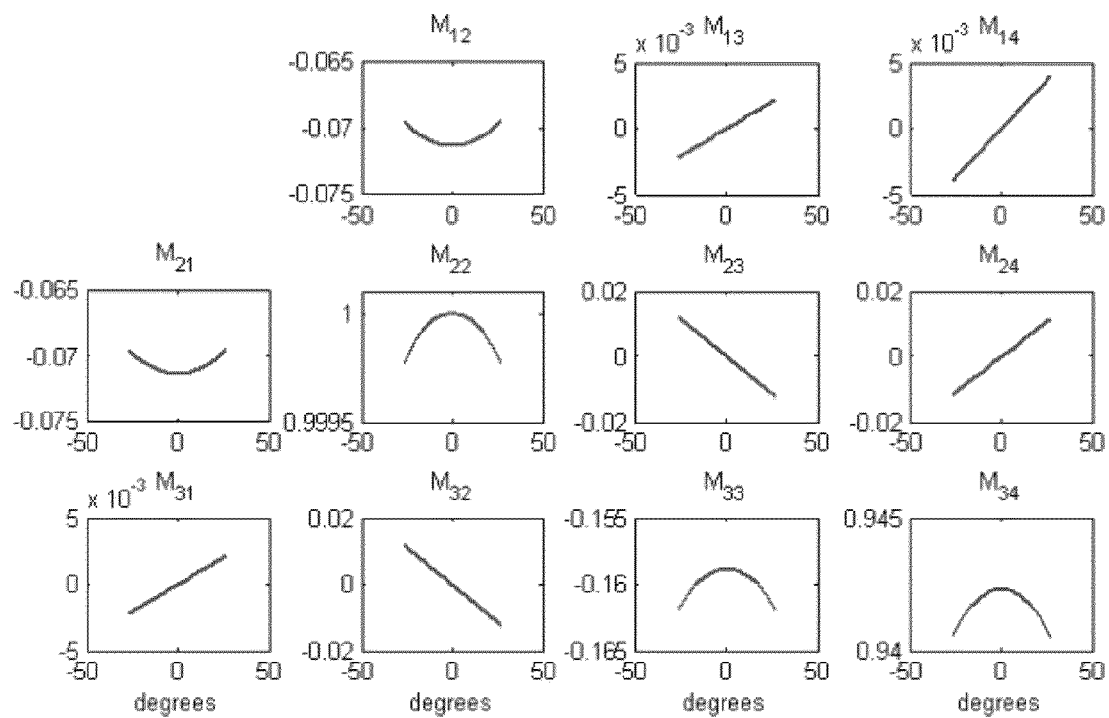
FIG. 11 illustrates a plot of the signal for each Mueller matrix element from FIG. 10 averaged over the wavelength range from 300 nm to 800 nm as a function of tilt $\delta_{SWA}$.

FIG. 11 illustrates a plot of the signal for each Mueller matrix element from FIG. 10 averaged over the wavelength range from 300 nm to 800 nm as a function of tilt $\delta_{SWA}$. As can be seen, over a large tilt range from −22° to +22°, the six off-diagonal elements $M_{13}$, $M_{14}$, $M_{23}$, $M_{24}$, $M_{31}$, and $M_{32}$ have a linear response to the tilting parameter $\delta_{SWA}$ and pass the origin (0, 0). In other words, when there is no tilting, i.e., the grating is symmetric, these off-diagonal Mueller matrix elements are essentially noise around zero. When the tilting is present, however, these off-diagonal elements start to deviate from zero level. The direction (negative or positive) of the deviation indicates the direction of the tilting (left or right). Moreover, the amplitude of the spectral deviation from zero is proportional to the amplitude of the tilting. Accordingly, this method enables detection of grating asymmetry without the need of structural and optical details and modeling procedure involved in typical OCD metrology.

As discussed with reference to FIG. 4, the off-diagonal coefficients of the Muller matrix may be analyzed (212 in FIG. 4) by fitting the measured off-diagonal coefficients of the Muller matrix to modeled off-diagonal coefficients of the Muller matrix or by fitting the measured off-diagonal coefficients of the Muller matrix to a calibrated linear response of measured or modeled off-diagonal coefficients of the Muller matrix.

Figure 12:
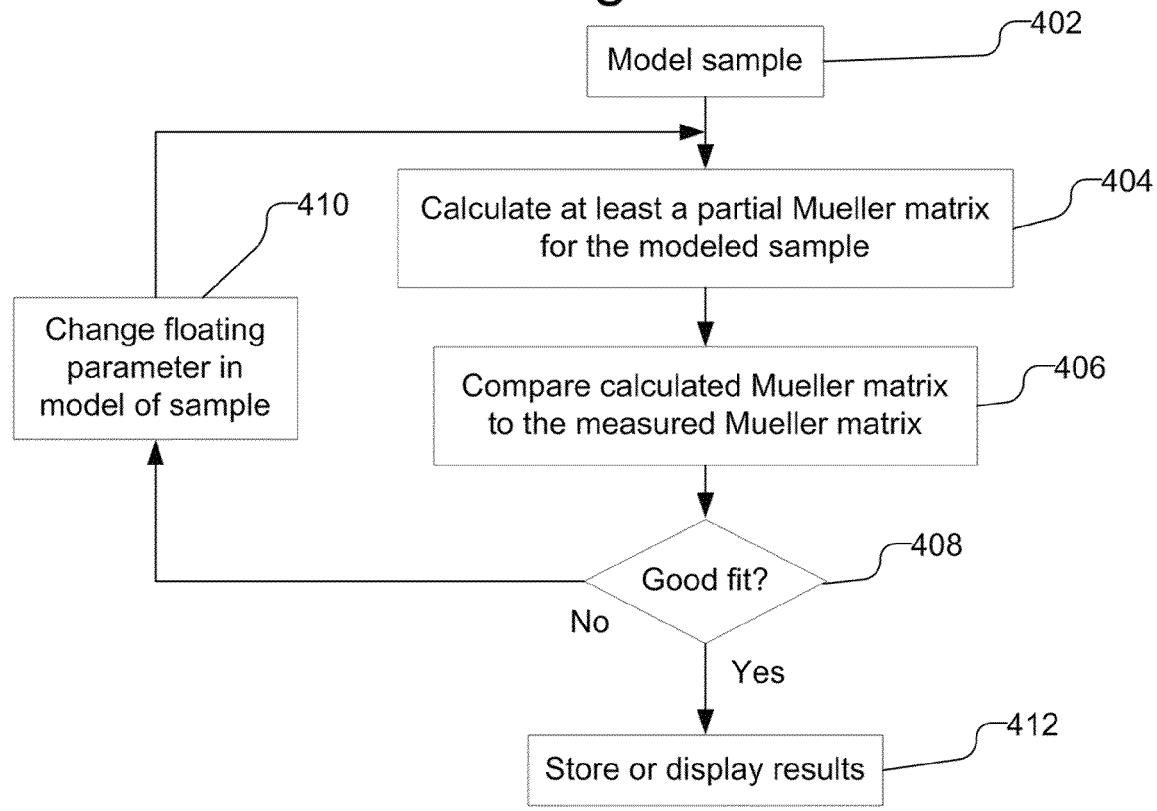
FIG. 12 illustrates analyzing the off-diagonal coefficients of the Muller matrix using a modeling technique.
Figure 13:
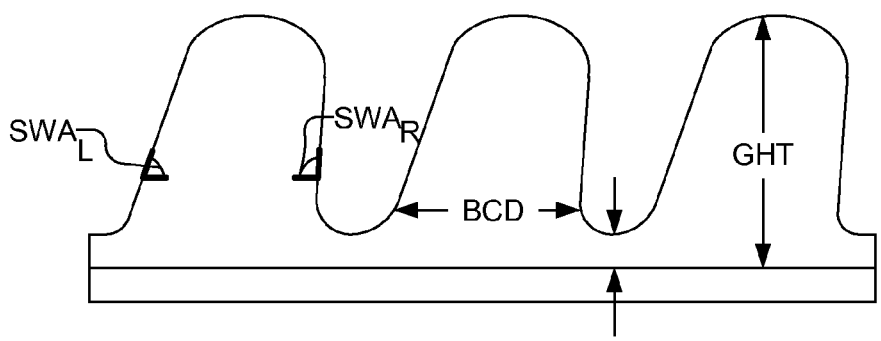
FIG. 13 illustrates a model for a structure with an asymmetry such as tilt.

FIG. 12 illustrates analyzing the off-diagonal coefficients of the Muller matrix using a modeling technique. As illustrated, a model of the sample is produced (402), e.g., using NanoDiffract™ from Nanometrics Incorporated. By way of example, the model for a structure with an asymmetry such as overlay error may include includes floating parameters that include the overlay error, CD, height and sidewall angle of the bottom and top grating elements, e.g., islands 302 and lines 304, as well as the thickness of any intervening layers. A model for a structure with an asymmetry such as tilt, such as that illustrated in FIG. 13 may include floating parameters including left and right sidewall angle ($SWA_L$, $SWA_R$), grating height (GHT), grating bottom critical dimension (BCD), and remaining layer thickness (RLT).

At least a partial Mueller matrix is calculated for the modeled sample, including the off-diagonal coefficients, such as $M_{13}$, $M_{31}$ and $M_{23}$, $M_{32}$ (404). The Muller matrix may be calculated using a rigorous electromagnetic model, such as Rigorous Couple Wave Analysis (RCWA), which may be performed by NanoDiffract™ from Nanometrics Incorporated. Elements in the calculated Mueller matrix, including at least the off-diagonal coefficients, are compared to the corresponding elements in the measured Mueller matrix, e.g., that was generated in step 210 in FIG. 4 (406). If desired, all of the elements or a partial set of the elements in the Mueller matrix that have been measured and calculated may be fitted. For example, the mean square error between the calculated and the measured Mueller matrix elements may be calculated, e.g., the sum of all the errors squared, and compared to a threshold value or is minimized. The goodness of fit is then determined (408), where an acceptable fit indicates that the modeled sample, including the modeled asymmetry as well as the other floating parameters, accurately describes the actual measured sample and the results are then stored or displayed (412). If the fit is not acceptable, the measured Mueller matrix is compared to a calculated Mueller matrix for a different model of the sample, e.g., in which one of the floating parameters has been changed (410). This process is repeated until an acceptable fit is achieved. It should be understood that the modeling and calculating the Mueller matrix may be performed in real time or a library of a number of models with varied floating parameters and the associated Mueller matrices may be pre-generated. FIG. 9 illustrates is an example of a set of measured and fit spectra for 11 Mueller matrix elements for an asymmetry measurement in the form of overlay error. As can be seen in FIG. 9, a good agreement for the experimental spectra and the theoretical spectra can be achieved and, thus, the overlay error can be determined.

Figure 14:
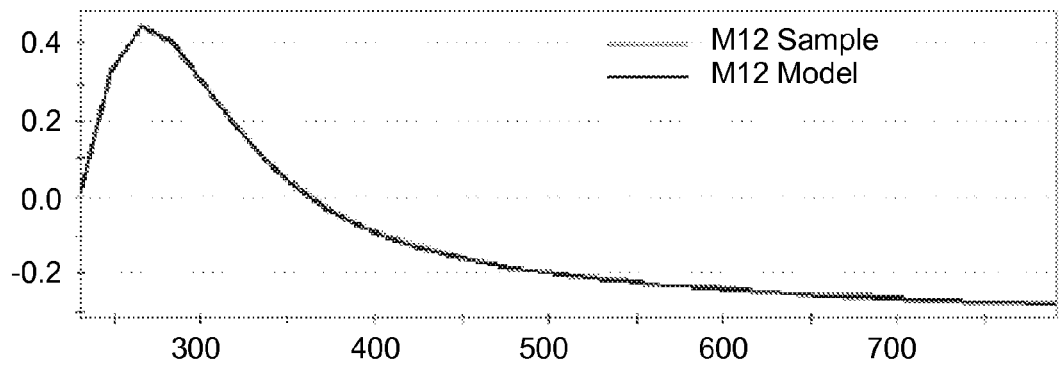
FIG. 14 illustrates a set of measured and fit spectra for 5 Mueller matrix elements, specifically $M_{12}$, $M_{33}$, $M_{34}$, $M_{23}$, and $M_{23}$ for an asymmetry measurement in the form of tilt.
Figure 14:
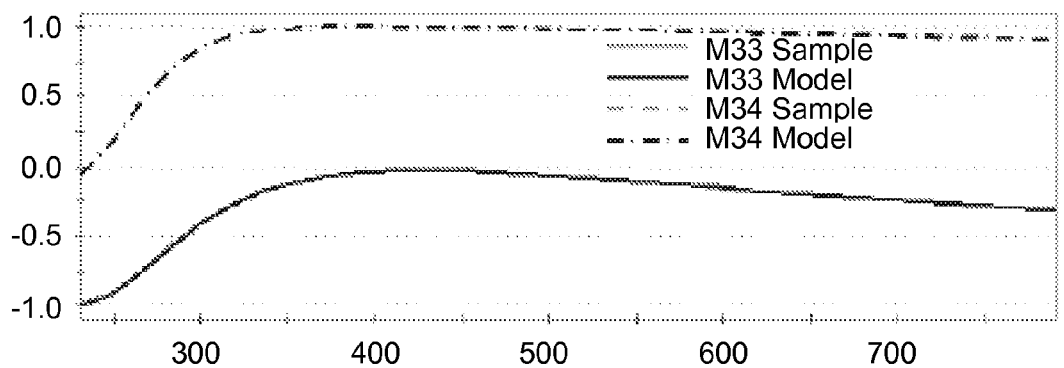
Figure 14:
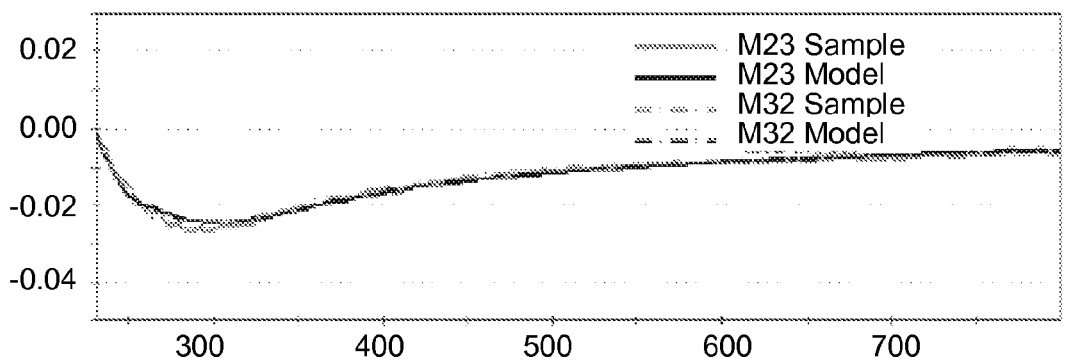

FIG. 14 illustrates a set of measured and fit spectra for 5 Mueller matrix elements, specifically $M_{12}$, $M_{33}$, $M_{34}$, $M_{23}$, and $M_{32}$ for an asymmetry measurement in the form of tilt. The measured data was obtained with a spectroscopic ellipsometer 100 and the fit spectra was generating using a model, such as that illustrated in FIG. 13, built to describe the grating structure using NanoDiffract software. As can be seen in FIG. 14, a good agreement for the experimental spectra and the theoretical spectra can be achieved. Thus, the individual sidewall angles $SWA_L$ and $SWA_R$ can be determined, from which the tilt $\delta_{SWA}$ can be calculated as the difference between the sidewall angles $SWA_L$ and $SWA_R$.

Figure 15:
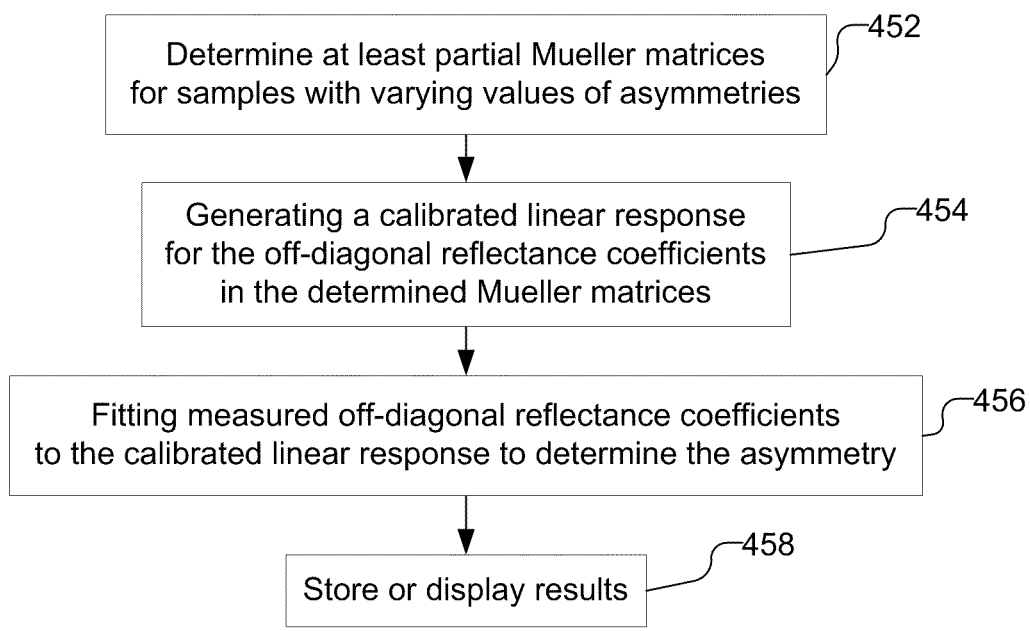
FIG. 15 illustrates analyzing the off-diagonal coefficients of the Muller matrix using a calibrated linear response.

FIG. 15 illustrates analyzing the off-diagonal coefficients of the Mueller matrix using a calibrated linear response. As illustrated, at least partial Mueller matrices are determined for a plurality of samples with varying values of the asymmetry, e.g., overlay error or tilt (452). By way of example, with an asymmetry such as overlay error, the overlay offsets for the samples may incrementally vary over ±15 nm range from the nominal offset. The range and incremental variation in the overlay offsets is dependent on the sample, including the CD, as well as the expected variation in overlay during production. For an asymmetry such as tilt, the sidewall angles or tilt $\delta_{SWA}$ of the sample may incrementally vary over a ±22° range from the symmetrical value of $\delta_{SWA}$ 0°, as illustrated in FIGS. 10 and 11. The Mueller matrices may be generated mathematically, e.g., through modeling and calculating the Mueller matrices, or empirically, e.g., by producing a number of samples with varying values of asymmetry with a known magnitude and measuring the Mueller matrices. For overlay error measurement, the effects of non-offset parameters, such as CD, height and sidewall angle, on linear combinations, e.g., $M_{13}+M_{31}$ are second order effects and can be neglected for small variations.

A calibrated linear response for the cross-reflection coefficients is generated based on the determined Mueller matrices (454). The calibrated linear response may be formed by generating a linear fit for the average spectral response to the asymmetry within the most sensitive portion of the spectrum or the entire spectrum. The linear response may be formed by the individual Mueller matrix coefficients, as illustrated in FIG. 11 or by combining the anti-symmetric cross-reflection coefficients (e.g., $M_{13}+M_{31}$ and/or $M_{23}+M_{32}$), as illustrated in FIG. 8. If desired, combination of the cross-reflection coefficients other than the sum may be used to form the linear response.

The off-diagonal coefficients from the measured Mueller matrix, e.g., that was generated in step 210 in FIG. 4, are then compared to the calibrated linear response to determine the value of the asymmetry for the measured sample (456) and the result is stored or displayed (458). To fit the off-diagonal coefficients from the measured Mueller matrix to the calibrated linear response, the spectral response for the same individual or combination of off-diagonal coefficients is produced for the measured Mueller matrix elements. Thus, for example, referring to FIG. 8, if the averaged spectral response for the combined anti-symmetric cross-reflection coefficients for the measured Mueller matrix is 0.005, the overlay shift would be approximately 8.9 nm.

Thus, by using an ellipsometer from which at least a portion of the Mueller matrix can be calculated, and in particular, the anti-symmetric cross-reflection coefficients can be determined, the alignment or overlay of two layers (or two patterns within a single layer) can be accurately measured. Moreover, the alignment or overlay can be determined using periodic structures of devices on the chip as the measurement target, as opposed to using special off-chip targets. Additionally, a single off-chip periodic target may be used to determine overlay, thereby reducing space requirements compared to conventional systems that use multiple periodic targets with variations in a designed in offset.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of determining asymmetry in a structure on a sample, the method comprising:
   producing polarized light that is incident on the structure on the sample;
   analyzing the light after the light is incident on the structure on the sample;
   passing the light through a rotating compensator before the light is incident on the sample or after the light is incident on the sample;
   detecting the light after analyzing the light;
   generating with a processor at least a partial Mueller matrix using the detected light;
   analyzing with the processor the Mueller matrix to determine the asymmetry in the structure wherein the asymmetry is determined without the use of light that is incident on and detected from a different structure.

2. The method of claim 1, further comprising passing the light through a rotating compensator before the light is incident on the sample or after the light is incident on the sample.

3. The method of claim 2, wherein the light is passed through a rotating compensator before the light is incident on the sample, the method further comprising passing the light after the light is incident on the sample through a second rotating compensator and generating a full Mueller matrix using the detected light.

4. The method of claim 1, wherein the sample is a semiconductor wafer and the structure is an in-chip structure.

5. The method of claim 1, wherein the sample is a semiconductor wafer and the structure is an off-chip target.

6. The method of claim 1, wherein the sample is a hard disk patterned media and the structure comprises at least one of patterned tracks and patterned islands.

7. The method of claim 1, wherein the sample is a microelectronic device.

8. The method of claim 1, wherein the structure includes a first periodic pattern that overlies a second periodic pattern and the determined asymmetry in the structure comprises overlay error.

9. The method of claim 1, wherein the structure includes a first pattern and a second pattern on the same level and the determined asymmetry in the structure comprises asymmetry between the first pattern and the second pattern.

10. The method of claim 1, wherein the structure includes a periodic pattern.

11. The method of claim 1, wherein the structure includes an isolated structure.

12. The method of claim 1, wherein the Mueller matrix is generated using the detected light without the use of light that is incident on and detected from a different structure.

13. The method of claim 1, wherein the polarized light comprises at least one of multiple wavelengths and multiple angles of incidence.

14. The method of claim 1, wherein cross-polarization reflectance coefficients in the Mueller matrix are analyzed to determine the asymmetry in the structure and the cross-polarization reflectance coefficients in the Mueller matrix comprise at least one set of anti-symmetric off-diagonal elements of the Mueller matrix.

15. The method of claim 1, wherein analyzing with the processor the Mueller matrix to determine the asymmetry of the structure comprises fitting with the processor the Mueller matrix elements to a rigorous electromagnetic model of the structure.

16. The method of claim 15, wherein the rigorous electromagnetic model is generated in at least one of real time and a library of pre-calculated and stored models.

17. The method of claim 1, wherein analyzing with the processor the Mueller matrix to determine the asymmetry of the structure comprises fitting with the processor cross-polarization reflectance coefficients in the Mueller matrix to a calibrated linear response.

18. The method of claim 1, wherein the determined asymmetry in the structure comprises asymmetric side wall angles.

19. The method of claim 1, wherein the determined asymmetry in the structure comprises tilt of the structure.

20. The method of claim 1, wherein the determined asymmetry is in two directions.

21. A method of determining asymmetry in an in-chip structure on a semiconductor wafer, the method comprising:
   illuminating the in-chip structure with polarized light;
   analyzing the specular light after the light interacts with the in-chip structure;
   detecting the analyzed light;
   generating with a processor at least a partial Mueller matrix using the detected light;
   fitting with the processor the Mueller matrix to at least one of a rigorous electromagnetic model of the in-chip structure and a calibrated linear response to determine the asymmetry in the in-chip structure.

22. The method of claim 21, further comprising variably altering the phase of at least one of the polarized light and the specular light.

23. The method of claim 21, further comprising variably altering the phase of the polarized light and the specular light and generating a full Mueller matrix using the detected light.

24. The method of claim 21, wherein the Mueller matrix is generated using the detected light from the in-chip structure without the use of light from a different set of structures.

25. The method of claim 21, wherein the polarized light comprises at least one of multiple wavelengths and multiple angles of incidence.

26. The method of claim 21, wherein illuminating the overlying in-chip structures, analyzing the specular light is performed using an ellipsometer.

27. The method of claim 21, wherein the Mueller matrix comprises at least one set of off-diagonal elements of the Mueller matrix.

28. The method of claim 21, wherein the rigorous electromagnetic model is generated in at least one of real time and a library of pre-calculated and stored models.

29. The method of claim 21, wherein the determined asymmetry in the structure comprises asymmetric side wall angles.

30. The method of claim 21, wherein the determined asymmetry in the structure comprises tilt of the structure.

31. The method of claim 21, wherein the structure includes a first periodic pattern that overlies a second periodic pattern and the determined asymmetry in the structure comprises overlay error.

32. The method of claim 21, wherein the structure includes a first pattern and a second pattern on the same level and the determined asymmetry in the structure comprises asymmetry between the first pattern and the second pattern.

33. The method of claim 21, wherein the structure includes a periodic pattern.

34. The method of claim 21, wherein the structure includes an isolated structure.

35. The method of claim 21, wherein the determined asymmetry is in two directions.

36. An apparatus for measuring asymmetry of a structure on a sample, the apparatus comprising:
a polarization state generator that produces polarized light to be incident on the structure;
a polarization state detector that analyzes and detects the light after the interacts with the structure and generates signals in response to the detected light;
a processor coupled to receive the signals from the polarization state detector;
memory coupled to the processor;
software held in the memory and run in the processor to generate at least a partial Mueller matrix using the signals from the polarization state detector and to fit the Mueller matrix to at least one of a rigorous electromagnetic model of the structure and a calibrated linear response to determine the asymmetry of the structure, wherein the asymmetry is determined without the use of light that is incident on and detected from a different structure.

37. The apparatus of claim 36, further comprising at least one rotating compensator between the polarization state generator and the polarization state detector.

38. The apparatus of claim 36, comprising two rotating compensators between the polarization state generator and the polarization state detector and wherein the software run in the processor causes the processor to generate a full Mueller matrix.

39. The apparatus of claim 36, wherein the polarization state generator produces polarized light having at least one of multiple wavelengths and multiple angles of incidence.

40. The apparatus of claim 36, wherein the Mueller matrix comprises at least one set of off-diagonal elements of the Mueller matrix.

41. The apparatus of claim 36, further comprising a library of pre-calculated rigorous electromagnetic model that is stored in the memory.

42. The apparatus of claim 36, wherein the software run in the processor causes the processor to generate the rigorous electromagnetic model in real time.

43. The apparatus of claim 36, further comprising a library of calibrated linear responses stored in the memory.

44. The apparatus of claim 36, wherein the determined asymmetry in the structure comprises asymmetric side wall angles.

45. The apparatus of claim 36, wherein the determined asymmetry in the structure comprises tilt of the structure.

46. The apparatus of claim 36, wherein the structure includes a first periodic pattern that overlies a second periodic pattern and the determined asymmetry in the structure comprises overlay error.

47. The apparatus of claim 36, wherein the structure includes a first pattern and a second pattern on the same level and the determined asymmetry in the structure comprises asymmetry between the first pattern and the second pattern.

48. The apparatus of claim 36, wherein the structure includes a periodic pattern.

49. The apparatus of claim 36, wherein the structure includes an isolated structure.

50. The apparatus of claim 36, wherein the sample is a microelectronic device.

51. The apparatus of claim 36, wherein the sample is a hard disk patterned media and the structure comprises at least one of patterned tracks and patterned islands.

52. The apparatus of claim 36, wherein the determined asymmetry is in two directions.

* * * * *